US010062463B2

(12) United States Patent
Inanami et al.

(10) Patent No.: US 10,062,463 B2
(45) Date of Patent: Aug. 28, 2018

(54) RADIATION PROTECTION EQUIPMENT AND RADIATION PROTECTION SYSTEM PROVIDED WITH RADIATION PROTECTION EQUIPMENT

(71) Applicant: INA MEDICAL DEVELOPMENT LABORATORY CO., LTD., Tokyo (JP)

(72) Inventors: Hirohiko Inanami, Tokyo (JP); Katsutoshi Otomo, Tokyo (JP)

(73) Assignee: INA MEDICAL DEVELOPMENT LABORATORY CO., LTD., Tokyo (JP)

(*) Notice: Subject to any disclaimer, the term of this patent is extended or adjusted under 35 U.S.C. 154(b) by 0 days.

(21) Appl. No.: 15/513,344

(22) PCT Filed: Sep. 17, 2015

(86) PCT No.: PCT/JP2015/004772
§ 371 (c)(1),
(2) Date: Mar. 22, 2017

(87) PCT Pub. No.: WO2016/047123
PCT Pub. Date: Mar. 31, 2016

(65) Prior Publication Data
US 2017/0309356 A1    Oct. 26, 2017

(30) Foreign Application Priority Data

Sep. 25, 2014  (JP) .................................. 2014-194643

(51) Int. Cl.
*A61B 6/10* (2006.01)
*A61N 5/10* (2006.01)
*G21F 3/00* (2006.01)

(52) U.S. Cl.
CPC ................ *G21F 3/00* (2013.01); *A61B 6/107* (2013.01)

(58) Field of Classification Search
CPC ....... A61B 6/107; A61B 6/0407; A61B 46/00; A61B 90/04; G21F 3/00
(Continued)

(56) References Cited

U.S. PATENT DOCUMENTS 5,006,718 A * 4/1991 Lenhart .................. A61B 6/107
                                                                250/515.1
5,417,225 A * 5/1995 Rubenstein ............ A61B 90/04
                                                                128/849
(Continued)

FOREIGN PATENT DOCUMENTS

JP          2-30095 U      2/1990
JP      2002-253547 A      9/2002
(Continued)

OTHER PUBLICATIONS

Notification of Transmittal of Translation of the International Preliminary Report on Patentability (Form PCT/IB/338) issued in counterpart International Application No. PCT/JP2015/004772 dated Apr. 6, 2017, with Forms PCT/IB/373, PCT/IB/326 and PCT/ISA/237. (13 pages).
(Continued)

*Primary Examiner* — David A Vanore
(74) *Attorney, Agent, or Firm* — Westerman, Hattori, Daniels & Adrian, LLP (57) ABSTRACT

An amount of radiation exposure of a medical staff is significantly reduced, and a large working area is ensured during an operation. A size of each component of a radiation protection equipment is reduced so as to decrease a weight thereof. The radiation protection equipment is provided, which can be installed within a short time period before an (Continued)

operation and easily put away after the operation. The radiation protection equipment, includes: a first protection sheet arranged on a periphery of a radiation source device and configured to shield radiation; a second protection sheet formed separately from the first protection sheet, arranged on a side of an operation table, and configured to shield radiation; and a third protection sheet formed separately from the first and second protection sheets, arranged on a periphery of a surgical field so as to expose the surgical field, and configured to shield the radiation.

8 Claims, 5 Drawing Sheets

(58) Field of Classification Search
USPC ..... 250/519.1, 515.1, 516.1, 505.1; 128/849, 128/846; 378/203
See application file for complete search history.

(56) References Cited

U.S. PATENT DOCUMENTS

| | | | | |
|---|---|---|---|---|
| 6,325,538 | B1* | 12/2001 | Heesch | A61B 6/107 128/846 |
| 7,608,847 | B2* | 10/2009 | Rees | G21F 3/02 2/117 |
| 7,638,784 | B2* | 12/2009 | Fox | G21F 1/125 250/505.1 |
| 8,716,687 | B2* | 5/2014 | Goldstein | A61B 6/107 128/849 |
| 2002/0109107 | A1* | 8/2002 | Goldstein | A61B 6/107 250/505.1 |
| 2006/0124871 | A1* | 6/2006 | Ballsieper | A61B 6/107 250/516.1 |
| 2012/0132217 | A1 | 5/2012 | Rees | |
| 2012/0241652 | A1* | 9/2012 | Jeschke | A61B 6/107 250/519.1 |

FOREIGN PATENT DOCUMENTS

| | | |
|---|---|---|
| JP | 2004-506911 A | 3/2004 |
| JP | 2006-526434 A | 11/2006 |
| JP | 2010-68990 A | 4/2010 |
| JP | 2010-521992 A | 7/2010 |
| JP | 2011-516165 A | 5/2011 |
| JP | 2013-512745 A | 4/2013 |
| WO | 02/15198 A1 | 2/2002 |
| WO | 2008/140486 A2 | 11/2008 |
| WO | 2009/124094 A2 | 10/2009 |

OTHER PUBLICATIONS

International Search Report dated Dec. 22, 2015, issued in counterpart International Application No. PCT/JP2015/004772 (2 pages).

Office Action dated Jul. 5, 2018, issued in counterpart Japanese patent application No. 2014-194643 (w/ English machine translation; 4 pages).

* cited by examiner

RADIATION PROTECTION EQUIPMENT AND RADIATION PROTECTION SYSTEM PROVIDED WITH RADIATION PROTECTION EQUIPMENT

TECHNICAL FIELD

The present invention relates to a radiation protection equipment configured to reduce the amount of radiation exposure of a medical staff, and a radiation protection system including the radiation protection equipment.

BACKGROUND ART

In Patent Literature 1, there is disclosed a radiation protection system configured to cover a patient on an X-ray table and separate a working area from an X-ray emitter having a C-shaped arm. The radiation protection system includes a radiation shielding wall, a radiation shielding screen on the X-ray table, and a flexible interface for radiation shielding, which is configured to connect the radiation shielding screen and the X-ray table to the radiation shielding wall. Further, the radiation shielding screen includes a plurality of screen support parts mounted to the X-ray table and radiation-resistant partition walls mounted to the screen support parts.

When the radiation shielding screen is in an extended state, the radiation shielding screen covers the X-ray table in the working area, and the radiation-resistant partition wall is interposed between the patient and a doctor. Further, when fluoroscopic treatment is performed, the radiation shielding screen is extended from a leg part of the X-ray table to a central abdominal portion of the patient. The radiation shielding screen can be folded when the screen support parts slide along the X-ray table.

The radiation shielding screen includes access ports so that the doctor can give treatment to the patient through use of a surgical instrument. Each access port is covered with a radiation shielding cloak attached to the radiation shielding screen. The radiation shielding cloak assists protection of the doctor giving treatment on a periphery of the X-ray table from radiation scattering through each access port.

CITATION LIST

Patent Literature

PTL 1: Japanese Patent No. 5016774

SUMMARY OF INVENTION

Technical Problem

According to the radiation protection system of Patent Literature 1, a medical staff can be protected from scattering radiation. However, for example, when an endoscopic spinal operation is performed, the working area is narrowed by the radiation shielding walls, with the result that there is difficulty in performing the operation. Further, the size of each component of the radiation protection system is large, and each component includes a shielding material containing lead or the like, with the result that the weight of the component becomes heavier. Further, it takes time to install the radiation protection system, and it requires labor to put away the components of the radiation protection system after the operation.

In order to solve the above-mentioned problem, according to one embodiment of the present invention, there is provided a radiation protection equipment, including: a first protection sheet arranged on a periphery of a radiation source device and configured to shield radiation; a second protection sheet formed separately from the first protection sheet, arranged on a side of an operation table, and configured to shield radiation; and a third protection sheet formed separately from the first protection sheet and the second protection sheet, arranged on a periphery of a surgical field so as to expose the surgical field, and configured to shield the radiation.

Further, according to another embodiment of the present invention, there is provided a radiation protection system, including: an imaging apparatus including a radiation source device and a detector; and the above-mentioned radiation protection equipment.

With this, the amount of radiation exposure of the medical staff can be significantly reduced, and a large working area can be ensured during an operation. Further, the size of each component of the radiation protection equipment can be reduced, and hence the weight thereof can be decreased. Further, the radiation protection equipment can be provided, which can be installed within a short time period before an operation and enables the components to be easily put away after the operation.

Further features of the present invention are apparent from the following description of exemplary embodiments with reference to the attached drawings.

DESCRIPTION OF EMBODIMENTS

Exemplary embodiments for carrying out the present invention are now described in detail with reference to the drawings. However, for example, the dimensions, materials, shapes, and relative positions of the components, which are described in the following embodiments, may be suitably set and changed based on the configuration of the system to which the present invention is applied or based on various conditions. Unless otherwise noted, the scope of the present invention is not limited to the embodiments specifically described herein. Vertical directions herein respectively correspond to an upward direction and a downward direction with respect to the direction of gravity. Further, horizontal directions correspond to directions parallel to a floor surface on which an operation table is installed.

[First Embodiment]

Figure 1:
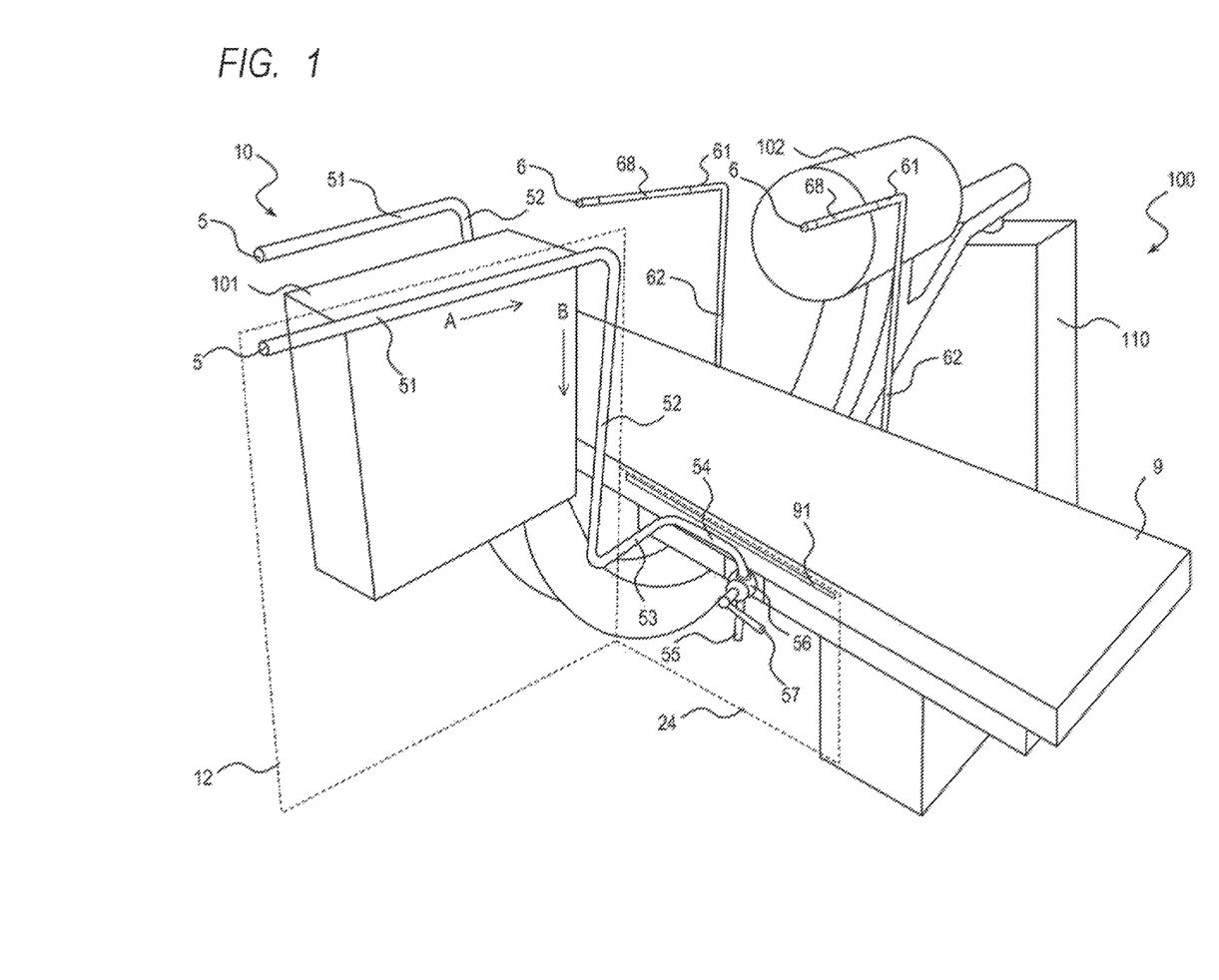
FIG. 1 is a schematic perspective view of a radiation protection system according to a first embodiment of the present invention.

A radiation protection system 100 according to a first embodiment of the present invention is described with reference to FIG. 1. FIG. 1 is a schematic perspective view of the radiation protection system 100 and is an illustration of a state as viewed from a foot side of an operation table 9. In FIG. 1, the right side of the operation table 9 corresponds to a foot side of a patient, and the left side of the operation table 9 corresponds to a head side of the patient.

As illustrated in FIG. 1, the radiation protection system 100 includes an imaging apparatus 110 and the operation table 9. The imaging apparatus 100 includes a radiation source device 101 and a detector 102. On the operation table 9, a patient to be subjected to an operation lies down. Further, in FIG. 1, first sheet support part 5 and second sheet support part 6, which are configured to support protection sheets of a radiation protection equipment 10, are illustrated. In FIG. 1, for convenience of description, illustration of the protection sheets is omitted, and only a second side surface sheet 12 of a first protection sheet and a foot side sheet 24 of a second protection sheet are illustrated with the dotted lines.

As the imaging apparatus 110, there are given various medical imaging apparatus using radiation. In the following, an X-ray imaging apparatus (surgical image pickup apparatus) is described below as an example. The imaging apparatus 110 includes the radiation source device 101 including an X-ray tube and an X-ray diaphragm device (not shown). The X-ray tube is configured to generate an X-ray through use of a high voltage to be supplied thereto. Further, the X-ray diaphragm device is configured to shield a part of the X-ray generated by the X-ray tube to control an irradiation field. Further, the imaging apparatus 110 includes the detector 102. The detector 102 is configured to detect radiation (X-ray), which is radiated from the radiation source device 101 and transmitted through the patient on the operation table 9, through conversion into an electric charge.

Further, the imaging apparatus 110 includes a C-shaped arm configured to support the radiation source device 101 and the detector 102. A imaging position may often be changed for a plurality of times in one operation. Therefore, the arm can perform various operations such as the movement in the vertical directions, the rotation around an axis of the arm, the slide movement along a curved direction of the arm, and the like.

When an operation is performed, an operator (medical staff) stands on the right side of FIG. 1, that is, the foot side of the patient with respect to the radiation source device 101, or on the left side of FIG. 1, that is, the head side of the patient with respect to the radiation source device 101 to perform the operation. Therefore, in order to protect the operator from radiation, the first protection sheet configured to shield radiation radiated from the radiation source device 101 is arranged on a periphery of the radiation source device 101. In FIG. 1, only the second side surface sheet 12 described later is illustrated with the dotted lines.

Further, in order to shield scattering radiation which comes out from the patient, the second protection sheet is arranged also between the operator and the patient, that is, on the side of the operation table 9. In FIG. 1, only the foot side sheet 24 described later is illustrated with the dotted lines. Further, in order to shield scattering radiation which comes out from the vicinity of a surgical field, a third protection sheet (not shown) is arranged also on the periphery of the surgical field.

In order to support those protection sheets, the radiation protection equipment 10 includes the first sheet support part 5 and the second sheet support part 6. The first sheet support part 5 includes a pair of sheet support parts arranged so that the radiation source device 101 is placed therebetween. Similarly, the second sheet support parts 6 include a pair of sheet support parts arranged so that the detector 102 is placed therebetween. Each of the sheet support parts includes a fixing part to be fixed to the operation table 9 and a pole serving as a main body. The first sheet support part 5 and the second sheet support part 6 have the same configuration except for the shape of the main body of the sheet support part. Therefore, the first sheet support part 5 is described below.

A fixing part 56 of the first sheet support part 5 may be formed of a pole clamp into which a lower end portion of the pole of the first sheet support part 5 can be inserted. The fixing part 56 includes a receiving part having a substantially U-shape in cross-section on the operation table 9 side. When the receiving part is inserted to a rail arranged on the operation table 9, the fixing part 56 is mounted to the operation table 9. With this, the fixing part 56 is mounted so as to be movable along a longitudinal direction of the operation table 9. Therefore, the distance from the radiation source device 101 or the detector 102 to the first sheet support part 5 can be appropriately adjusted.

Further, an insertion hole into which the lower end portion of the pole can be inserted is formed in the fixing part 56. When a lever 57 is rotated after the lower end portion is inserted into the insertion hole, the lower end portion can be held and fixed in the fixing part 56. Further, when the lever 57 is loosened, the first sheet support part 5 can be moved along the vertical directions. With this, the height of the first sheet support part 5 with respect to the operation table 9 can be appropriately adjusted.

Further, the first sheet support part 5 includes a first extension part 51 extending in the horizontal direction A (an emitting direction of radiation) of FIG. 1. Further, the first sheet support part 5 includes a second extension part 52 continuing from the first extension part 51, and the second extension part 52 extends in the vertical direction B (a downward direction) of FIG. 1. Further, the first sheet support part 5 can be rotated about the fixing part 56 in the horizontal direction. When the lever 57 is loosened, the orientation of the first extension part 51 can be changed, and the position thereof can be appropriately adjusted.

The pole of the first sheet support part 5 can be formed by bending a stainless steel pipe having a diameter of from 13 mm to 14 mm and a length of 145 cm. In the first sheet support part 5, one sheet support part arranged on the foot side of the patient includes the first extension part 51 of 45 cm and the second extension part 52 of 50 cm formed so as to be bent downward at 90° from the first extension part 51. Further, the one sheet support part includes a third extension part 53 of 20 cm formed so as to be bent in the emitting direction at 90° from the second extension part 52, a fourth extension part 54 of 15 cm formed so as to be bent toward the foot side at 90° along the longitudinal direction of the operation table 9, and a fifth extension part 55 of 15 cm formed so as to be bent downward at 90° from the fourth extension part 54.

Further, another sheet support part of the first sheet support part 5 has a shape symmetrical to that of the one sheet support part with respect to the radiation source device 101. That is, the another sheet support part includes the first extension part 51 of 45 cm, the second extension part 52 of 50 cm formed so as to be bent downward at 90° from the first extension part, the third extension part 53 of 20 cm formed so as to be bent in the emitting direction at 90° from the second extension part 52, the fourth extension part 54 of 15 cm formed so as to be bent toward the head side at 90° along the longitudinal direction of the operation table 9, and the fifth extension part 55 of 15 cm formed so as to be bent downward at 90° from the fourth extension part 54.

Meanwhile, the pole of the second sheet support part 6 can be formed by bending a stainless steel pipe having a diameter of from 13 mm to 14 mm and a length of 110 cm. Each pole of the second sheet support part 6 has a substantially L-shape. That is, the second sheet support part 6 includes a first extension part 61 of 45 cm extending in the emitting direction of radiation, and a second extension part 62 of 65 cm formed so as to be bent downward at 90° from the first extension part 61. A hook-and-loop fastener 68 configured to mount the protection sheet is mounted to the first extension part 61 of the second sheet support part 6.

Further, an end portion of the second extension part 62 of the second sheet support part 6 is also inserted into the fixing part (pole clamp) mounted to the operation table 9 and fixed. The fixing parts of the first sheet support part 5 and the second sheet support part 6 are not limited to pole clamps. For example, the fixing part can also be formed of a pin that can be inserted into a hole formed in the pole of the sheet support part.

Figure 2A:
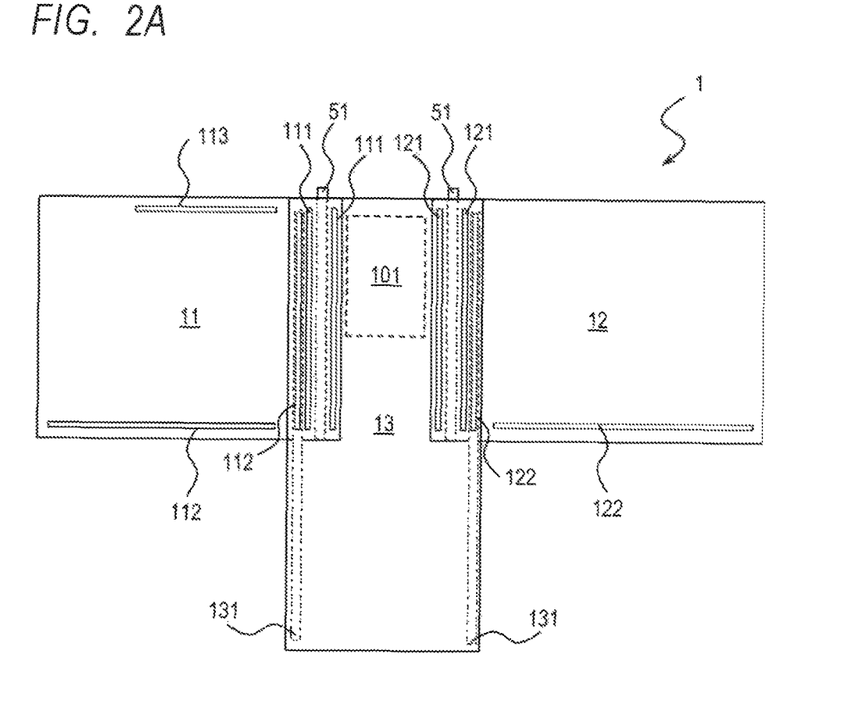
FIG. 2A is a view for illustrating a developed state of a first protection sheet.
Figure 2B:
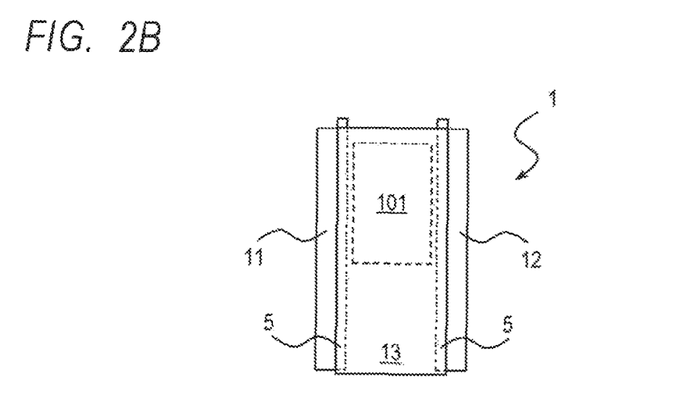
FIG. 2B is a view for illustrating a mounted state of the first protection sheet.
Figure 3A:
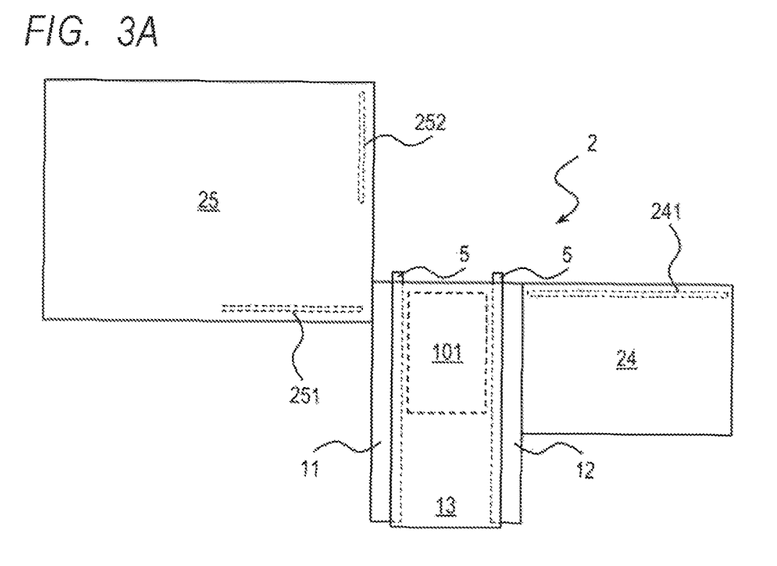
FIG. 3A is a view for illustrating the first protection sheet and a developed state of a second protection sheet.
Figure 3B:
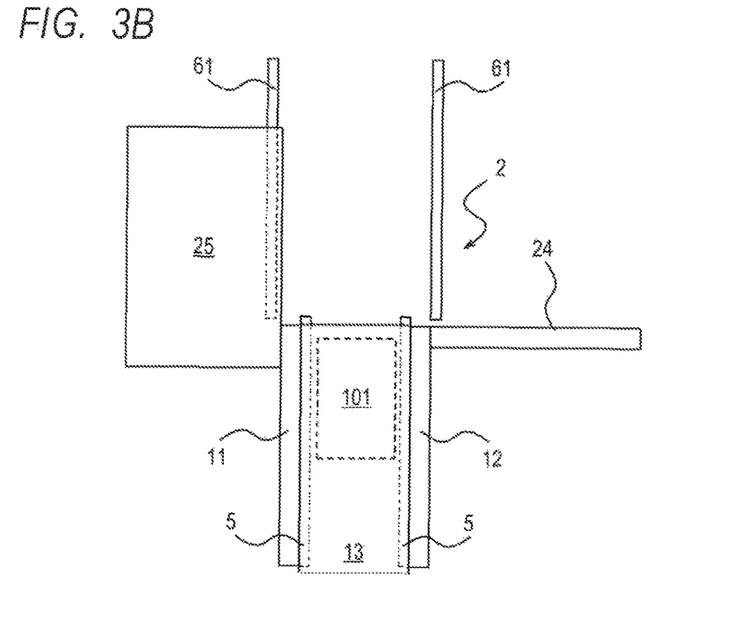
FIG. 3B is a view for illustrating mounted states of the first and second protection sheets.
Figure 4:
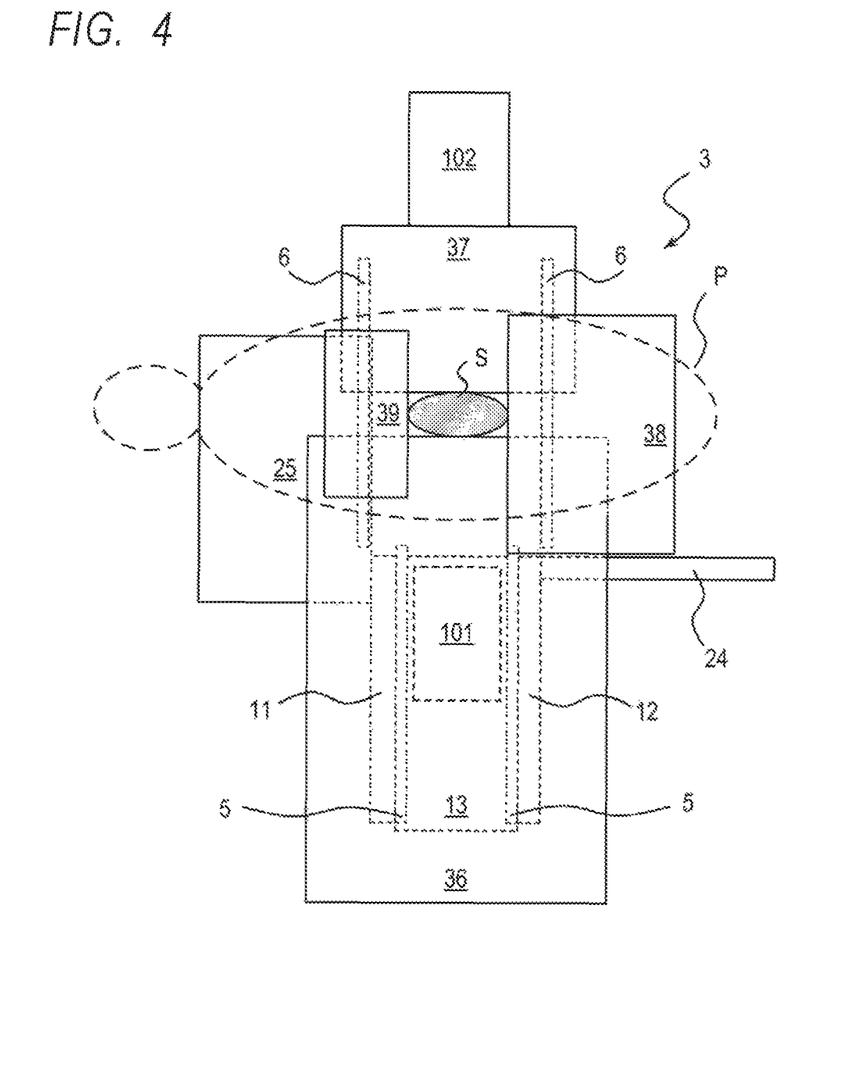
FIG. 4 is a view for illustrating a third protection sheet in a developed state.

Subsequently, mounting of the first to third protection sheets is described with reference to FIG. 2A, FIG. 2B, FIG. 3A, FIG. 3B, and FIG. 4. FIG. 2A, FIG. 3A, and FIG. 4 are views for illustrating states of the protection sheets in a developed state, as viewed from above. The right side corresponds to the foot side of the patient, and the left side corresponds to the head side of the patient. Further, FIG. 2B and FIG. 3B are views for illustrating the protection sheets in a hanging state after being mounted, as viewed from above.

The radiation protection equipment 10 includes a first protection sheet 1 arranged on the periphery of the radiation source device 101 and configured to shield radiation, a second protection sheet 2 arranged between the operator and the patient and configured to shield radiation, and a third protection sheet 3 arranged on the periphery of a surgical field so as to expose the surgical field and configured to shield radiation. The first protection sheet 1, the second protection sheet 2, and the third protection sheet 3 are formed separately from each other.

Each protection sheet includes a surface material and a shielding material for radiation. The shielding material is arranged on an inner side of the surface material. For example, the protection sheet is formed of a sheet having a lead equivalent of 0.25 mmPb and has a shielding ability to shield radiation by about 80% to about 99%.

When such protection sheet is folded and stored, there is a risk in that the shielding material in a folded portion may be damaged to cause degradation of the shielding ability. Therefore, even when the protection sheet has a large size, the protection sheet cannot be folded, and it is necessary to ensure a large storage space. In this respect, according to the first embodiment, the first protection sheet 1, the second protection sheet 2, and the third protection sheet 3 are formed separately from each other. With this, the size of each protection sheet can be reduced, thereby being capable of stacking the protection sheets for storage without folding the protection sheets. Therefore, it is not necessary to ensure a large storage space, and there is no risk of damage to the shielding material in the folded portion.

Further, the first protection sheet 1, the second protection sheet 2, and the third protection sheet 3 are formed separately from each other, and hence the weight of each protection sheet can be reduced. For example, in the case of a protection sheet having dimensions of 200 cm×70 cm, the weight of the protection sheet is from about 5.4 kg to about 10.0 kg, and it cannot be easily mounted. Meanwhile, in the case of a protection sheet having dimensions of 100 cm×70 cm, the weight of the protection sheet is a half of the protection sheet having dimensions of 200 cm×70 cm, and it can be relatively easily mounted.

When the radiation protection equipment 10 is mounted to the operation table 9, the second sheet support part 6 (FIG. 1) is first mounted to the operation table 9. The second sheet support part 6 is mounted so that the first extension part 61 is positioned above the operation table 9 (above a patient). Then, the first sheet support part 5 (FIG. 1) is mounted to the operation table 9. The first sheet support part 5 is mounted so that the radiation source device 101 is placed between the first extension parts 51.

Next, as illustrated in FIG. 2A, the first protection sheet 1 (first protection sheet set) is arranged on the periphery of the radiation source device 101. The first protection sheet 1 includes a first side surface sheet 11 facing a first side surface of the radiation source device 101, a second side surface sheet 12 facing a second side surface on an opposite side to the first side surface of the radiation source device 101, and a back surface sheet 13 facing a back surface and an upper surface of the radiation source device 101. The back surface of the radiation source device 101 is a surface on an opposite side to a side facing the detector 102. The first side surface sheet 11, the second side surface sheet 12, and the back surface sheet 13 can be formed separately from each other. With this, the size of each protection sheet can be further reduced, and the weight of each protection sheet can be even further decreased.

The first side surface sheet 11 is mounted to the first extension part 51 of the first sheet support part 5. The first side surface sheet 11 has a rectangular shape having dimensions of 100 cm×70 cm, and a pair of upper edge hook-and-loop fasteners 111 are arranged in an upper end portion of the first side surface sheet 11. When mounting the first side surface sheet 11, the pair of upper edge hook-and-loop fasteners 111 are first joined to each other so that the upper end portion is bent to have a substantially ring shape in cross-section. Then, the first extension part 51 of the one sheet support part of the first sheet support part 5 is inserted into an inner side of the ring shape, to thereby mount the first side surface sheet 11 to the first extension part 51.

Similarly, the second side surface sheet 12 is mounted to the first extension part 51. The second side surface sheet 12 is a rectangular protection sheet having dimensions of 110 cm×70 cm, and a pair of upper edge hook-and-loop fasteners 121 are arranged in an upper end portion of the second side surface sheet 12. When mounting the second side surface sheet 12, the pair of upper edge hook-and-loop fasteners 121 are first joined to each other so that the upper end portion is bent to have a substantially ring shape in cross-section. Then, the first extension part 51 of the another sheet support part of the first sheet support part 5 is inserted into an inner side of the ring shape, to thereby mount the second side surface sheet 12 to the first extension part 51.

Further, the back surface sheet 13 is mounted to the first side surface sheet 11 and the second side surface sheet 12. The back surface sheet 13 is a rectangular protection sheet having dimensions of 130 cm×30 cm. A pair of side edge hook-and-loop fasteners 131 are arranged on back surfaces of both side edge portions of the back surface sheet 13. Further, a side edge hook-and-loop fastener 112 is arranged on the first side surface sheet 11, and a side edge hook-andloop fastener 122 is arranged also on the second side surface sheet 12. When the back surface sheet 13 is mounted to the first side surface sheet 11 and the second side surface sheet 12, the side edge hook-and-loop fasteners 131 of the back surface sheet 13 are joined to the side edge hook-and-loop fastener 112 of the first side surface sheet 11 and to the side edge hook-and-loop fastener 122 of the second side surface sheet 12. The side edge hook-and-loop fasteners 131 arranged on the back surface are illustrated with the dotted lines.

As illustrated in FIG. 2B, the first side surface sheet 11 and the second side surface sheet 12, which have been mounted, are positioned on both sides of the radiation source device 101. The first side surface sheet 11 and the second side surface sheet 12 are supported by the first sheet support part 5, and hang down on the floor surface side. Further, the back surface sheet 13, which has been mounted, is positioned on a back side and an upper side of the radiation source device 101. The back surface sheet 13 is supported by the first sheet support part 5 through intermediation of the first side surface sheet 11 and the second side surface sheet 12, and hangs down on the floor surface side. Further, end portions of the first side surface sheet 11, the second side surface sheet 12, and the back surface sheet 13 are superposed and joined to each other so that the first side surface sheet 11, the second side surface sheet 12, and the back surface sheet 13 are arranged without a gap.

Next, the second protection sheet 2 (second protection sheet set) is arranged between the operator and the patient (operation table 9). As illustrated in FIG. 3A, the second protection sheet 2 includes the foot side sheet 24 arranged on the foot side of the patient with respect to the radiation source device 101 and a head side sheet 25 arranged on the head side of the patient with respect to the radiation source device 101. The foot side sheet 24 and the head side sheet 25 can be formed separately from each other. With this, the size of each protection sheet can be even further reduced, and the weight thereof can be even further decreased.

The foot side sheet 24 is mounted to the side of the operation table 9. The foot side sheet 24 is a rectangular protection sheet having dimensions of 50 cm×70 cm, and an upper edge hook-and-loop fastener 241 is arranged in an upper end portion of the foot side sheet 24. When mounting the foot side sheet 24, the upper edge hook-and-loop fastener 241 is joined to a hook-and-loop fastener 91 (FIG. 1) arranged on the operation table 9. The upper edge hook-and-loop fastener 241 arranged on the back surface is illustrated with the dotted lines.

The head side sheet 25 is mounted to the first side surface sheet 11 and to the first extension part 61 of the second sheet support part 6. The head side sheet 25 is a rectangular protection sheet having dimensions of 110 cm×80 cm. A side edge hook-and-loop fastener 251 is arranged on a back side of a side edge portion of the head side sheet 25. Further, the hook-and-loop fastener 68 (FIG. 1) is arranged on the first extension part 61. Further, an upper edge hook-and-loop fastener 252 is arranged on a back side of an upper edge portion of the head side sheet 25. Further, a side edge hook-and-loop fastener 113 (FIG. 2A) is arranged in a side edge portion of the first side surface sheet 11 on the operation table 9 side.

When mounting the head side sheet 25, the side edge hook-and-loop fastener 251 is joined to the side edge hook-and-loop fastener 113 of the first side surface sheet 11. At the same time, the upper edge hook-and-loop fastener 252 is joined to the hook-and-loop fastener 68 of the first extension part 61. The side edge hook-and-loop fastener 251 and the upper edge hook-and-loop fastener 252 arranged on the back surface are illustrated with the dotted lines.

As illustrated in FIG. 3B, the head side sheet 25, which has been mounted, is supported by the first extension part 61 and the first side surface sheet 11. Further, the head side sheet 25 is arranged between the first side surface sheet 11 and the operation table 9 so that a part of the head side sheet 25 is positioned on the side of the operation table 9, and another part of the head side sheet 25 covers a part of the patient. Further, end portions of the foot side sheet 24 and the second side surface sheet 12 are superposed on each other, and end portions of the head side sheet 25 and the first side surface sheet 11 are superposed on each other. Thereby, the foot side sheet 24 and the second side surface sheet 12 are arranged without a gap, and the head side sheet 25 and the first side surface sheet 11 are arranged without a gap. The second protection sheet 2 may be arranged only on one side. However, a plurality of medical staffs are generally involved in an operation, and hence the second protection sheet 2 is arranged on both sides of the radiation source device 101.

Next, as illustrated in FIG. 4, the third protection sheet 3 (third protection sheet set) is arranged on the periphery of a surgical field S. The third protection sheet 3 includes at least two sheets that are combined so as to expose a rectangular region. The third protection sheet 3 according to the first embodiment includes four protection sheets (first to fourth surgical field sheets) that surround the surgical field S. The first to fourth surgical field sheets are formed separately from each other. With this, the size of each protection sheet can be even further reduced, and the weight thereof can be even further decreased. The surgical field S is a rectangular region having a side of, for example, from 15 cm to 45 cm.

Further, an edge of each of the first to fourth surgical field sheets on the surgical field S side defines each side of the rectangular surgical field S. After the third protection sheet 3 is arranged, the third protection sheet 3 is covered with a sterilized cover cloth (not shown), and the cover cloth is attached to the body of the patient with a tape. Therefore, the cover cloth is positioned between the third protection sheet 3 and the surgical field S. With this, during an operation, the third protection sheet 3 is prevented from being placed over the surgical field S. Further, the third protection sheet 3, in place of the cover cloth, may be sterilized and attached to the body of the patient. Further, the third protection sheet 3 may be accommodated into a sterilized cover and attached to the body of the patient.

When the third protection sheet 3 is arranged, a first surgical field sheet 36 is first placed on the first sheet support part 5 and the second sheet support part 6. The first surgical field sheet 36 is a rectangular protection sheet having dimensions of 140 cm×90 cm. When the first surgical field sheet 36 is arranged, the first surgical field sheet 36 is arranged so as to cover the radiation source device 101 and to be placed over a part of a patient P.

Further, the first surgical field sheet 36 is superposed on the first protection sheet 1 (first side surface sheet 11, second side surface sheet 12, and back surface sheet 13) and on a part of the head side sheet 25. That is, the first surgical field sheet 36 is placed on the first sheet support part 5 through intermediation of the first side surface sheet 11, the second side surface sheet 12, and the back surface sheet 13. Further, the first surgical field sheet 36 is placed on the second sheet support part 6 through intermediation of the head side sheet 25.

Subsequently, the second surgical field sheet 37 is mounted to the second sheet support part 6. In this case, the second surgical field sheet 37 is arranged so as to be placed over a part of the patient P. The second surgical field sheet 37 is a rectangular protection sheet having dimensions of 70 cm×50 cm, and a hook-and-loop fastener (not shown) is arranged in a part of the second surgical field sheet 37. When mounting the second surgical field sheet 37, the hook-and-loop fastener of the second surgical field sheet 37 is joined to the hook-and-loop fastener 68 of the first extension part 61. With this, the second surgical field sheet 37 is mounted to the second sheet support part 6.

Subsequently, a third surgical field sheet 38 is placed on the second sheet support part 6. The third surgical field sheet 38 is a rectangular protection sheet having dimensions of 50 cm×60 cm. When the third surgical field sheet 38 is arranged, the third surgical field sheet 38 is arranged so as to be superposed on a part of the first surgical field sheet 36 and the second surgical field sheet 37 and placed over a part of the patient P. That is, the third surgical field sheet 38 is placed on the first sheet support part 5 through intermediation of the first surgical field sheet 36 and placed on the second sheet support part 6 through intermediation of the second surgical field sheet 37.

A fourth surgical field sheet 39 is placed on the second sheet support part 6. The fourth surgical field sheet 39 is a rectangular protection sheet having dimensions of 50 cm×25 cm. When the fourth surgical field sheet 39 is arranged, the fourth surgical field sheet 39 is arranged so as to be superposed on a part of the first surgical field sheet 36, the second surgical field sheet 37, and the head side sheet 25 and placed over a part of the patient P. That is, the fourth surgical field sheet 39 is placed on the second sheet support part 6 through intermediation of the second surgical field sheet 37 and the head side sheet 25.

Thus, the third protection sheet 3 includes a plurality of protection sheets which are formed separately from each other and surround the surgical field S, and hence the third protection sheet 3 can expose the surgical field S having suitable area and shape. That is, the area and shape of the surgical field S to be exposed can be changed by changing the degree of superposition of the first surgical field sheet 36, the second surgical field sheet 37, the third surgical field sheet 38, and the fourth surgical field sheet 39. Thus, even when the area of the surgical field S varies depending on the body shape of the patient or the operation type, the surgical field S can be surrounded by the protection sheets.

With the radiation protection equipment 10 according to the first embodiment, the amount of radiation exposure of the medical staff can be significantly reduced. Specifically, as a result of measurement for the amount of radiation exposure through use of the radiation protection equipment 10, it has been found that the effective dose equivalent can be reduced to about 1/20 of that of the related art.

Further, with the radiation protection equipment 10 according to the first embodiment, a large working area can be ensured during an operation. Further, the size of each component of the radiation protection equipment 10 can be reduced, thereby being capable of decreasing the weight thereof. Further, the radiation protection equipment 10 can be installed within a short time period before the operation, and each component can be easily put away after the operation.

[Second Embodiment]

Figure 5:
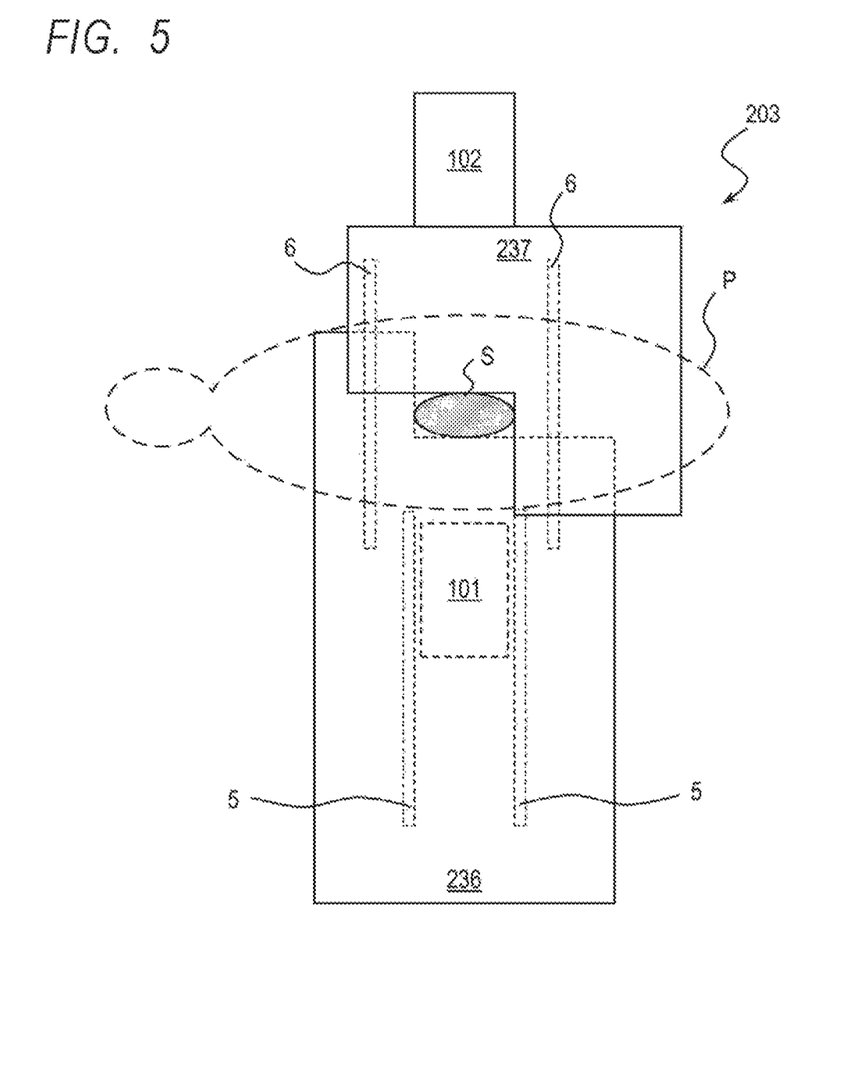
FIG. 5 is a view for illustrating a third protection sheet in a developed state according to a second embodiment of the present invention.

Subsequently, a radiation protection equipment 10 according to a second embodiment of the present invention is described with reference to FIG. 5. FIG. 5 is a view for illustrating mounting of a third protection sheet 203, and the first protection sheet 1 and the second protection sheet 2 are not shown. Further, FIG. 5 is a view for illustrating the third protection sheet 203 in a developed state as viewed from above. In FIG. 5, the right side corresponds to the foot side of the patient, and the left side corresponds to the head side of the patient.

In the description of the second embodiment, differences from the first embodiment are described. The components described in the first embodiment are denoted by the same reference symbols, and descriptions thereof are therefore omitted. Unless otherwise noted, the components denoted by the same reference symbols have substantially the same operation and function, and actions and effects thereof are also substantially the same.

In the second embodiment, the shape of the third protection sheet 203 is different from that of the first embodiment. Specifically, the third protection sheet 203 includes two protection sheets including a first surgical field sheet 236 and a second surgical field sheet 237, which surround the surgical field S. The first surgical field sheet 236 and the second surgical field sheet 237 both have a substantially L-shape. Also with the third protection sheet 203 according to the second embodiment, the first surgical field sheet 236 and the second surgical field sheet 237 can be combined so as to expose a rectangular region.

Further, the first surgical field sheet 236 and the second surgical field sheet 237 are formed separately from each other. With this, the size of each protection sheet can be even further reduced, and the weight thereof can be even further decreased. Two edges on the surgical field S side of each of the first surgical field sheet 236 and the second surgical field sheet 237 define each side of the rectangular surgical field S. Also in the second embodiment, the third protection sheet 203 is covered with a sterilized cover cloth (not shown), and the cover cloth is attached to the body of the patient P with a tape. Further, the third protection sheet 203, in place of the cover cloth, may be sterilized and attached to the body of the patient. Further, the third protection sheet 203 may be accommodated into a sterilized cover and attached to the body of the patient.

When the third protection sheet 203 is arranged, the first surgical field sheet 236 is first placed on the first sheet support part 5 and mounted to the second sheet support part 6. The first surgical field sheet 236 is a substantially L-shaped protection sheet, and has a shape obtained by cutting away a rectangle having dimensions of 30 cm×60 cm from a rectangle having dimensions of 180 cm×90 cm. Further, a hook-and-loop fastener (not shown) is arranged in a part of the first surgical field sheet 236.

When the first surgical field sheet 236 is arranged, the first surgical field sheet 236 is arranged so as to cover the radiation source device 101 and to be superposed on the first protection sheet 1 (not shown) and a part of the foot side sheet 25 (not shown), and placed over a part of the patient P. That is, the first surgical field sheet 236 is placed on the first sheet support part 5 through intermediation of the first protection sheet 1. At the same time, the hook-and-loop fastener of the first surgical field sheet 236 is joined to the hook-and-loop fastener 68 of the second sheet support part 6. With this, the first surgical field sheet 236 is mounted to the second sheet support part 6.

Subsequently, the second surgical field sheet 237 is mounted to the second sheet support part 6. In this case, the second surgical field sheet 237 is arranged so as to be superposed on a part of the foot side sheet 25 (not shown) and placed over a part of the patient P. The second surgical field sheet 237 is a substantially L-shaped protection sheet, and has a shape obtained by cutting away a rectangle having dimensions of 50 cm×40 cm from a rectangle having dimensions of 100 cm×85 cm. Further, a hook-and-loop fastener (not shown) is arranged in a part of the second surgical field sheet 237. When mounting the second surgical field sheet 237, the hook-and-loop fastener of the second surgical field sheet 237 is joined to the hook-and-loop fastener 68 of the second sheet support part 6. With this, the second surgical field sheet 237 is mounted to the second sheet support part 6.

As described above, the third protection sheet 203 according to the second embodiment includes a plurality of protection sheets which are formed separately from each other and surround the surgical field S, and hence the third protection sheet 3 can expose the surgical field S having suitable area and shape. That is, the area and shape of the surgical field S to be exposed can be changed by changing the degree of superposition of the first surgical field sheet 236 and the second surgical field sheet 237. Thus, even when the area of the surgical field S varies depending on the body shape of the patient or the operation type, the surgical field S can be surrounded by the protection sheets.

Also with the radiation protection equipment 10 according to the second embodiment, the amount of radiation exposure of the medical staff can be significantly reduced, and a large working area can be ensured during an operation. Further, the size of each component of the radiation protection equipment 10 can be reduced, thereby being capable of decreasing the weight thereof. Further, the radiation protection equipment 10 can be installed within a short time period before the operation, and each component can be easily put away after the operation.

The present invention is described above by way of each embodiment, but the present invention is not limited to the above-mentioned embodiments. The present invention also encompasses the invention modified within the scope of the present invention, and the invention equivalent to the present invention. Each of the above-mentioned embodiments and each modification example can be appropriately combined within the scope of the present invention.

For example, the size of each protection sheet can be suitably changed depending on the dimensions and the like of the imaging apparatus 110. In particular, the lengths of the first side surface sheet 11 and the second side surface sheet 12 can be appropriately set depending on the height of the radiation source device 101. Further, the first protection sheet 1 may include four or more protection sheets or two protection sheets. The second protection sheet 2 may include three or more protection sheets. Further, the third protection sheet 3 may include five or more protection sheets. Further, the first surgical field sheet 36 of the third protection sheet 3 covers an upper portion of the radiation source device 101, but the first surgical field sheet 36 may be formed to dimensions that do not cover the radiation source device 101.

Further, the first sheet support part 5 can be formed to a substantially L-shape in the same manner as in the second sheet support part 6. Further, it is only necessary that the first sheet support part 5 and the second sheet support part 6 have a shape capable of supporting the protection sheets, and the first sheet support part 5 and the second sheet support part 6 may be formed of a pipe curved in an arc shape. Further, the first sheet support part 5 and the second sheet support part 6 may be formed of a stainless steel plate having a planar shape. However, a large sheet support part such as a screen has a risk of falling down. Thus, it is preferred that a relatively small sheet support part capable of being fixed to the operation table 9 be employed.

Further, means for mounting the protection sheet to the sheet support part is not limited to the hook-and-loop fastener. The protection sheet can be mounted through use of means such as a snap button, a belt, and an adhesive tape. Further, a tubular mounting part may be arranged on the protection sheet so that the protection sheet is mounted to the sheet support part with the mounting part.

This application claims the benefit of priority from Japanese Patent Application No. 2014-194643, filed on Sep. 25, 2014, the content of which is incorporated herein by reference.

REFERENCE SIGNS LIST

1: first protection sheet, 2: second protection sheet, 3: third protection sheet, 5: first sheet support part, 6: second sheet support part, 9: operation table, 10: radiation protection equipment, 11: first side surface sheet, 12: second side surface sheet, 13: back surface sheet, 51: first extension part, 52: second extension part, 56: fixing part, 61: first extension part, 62: second extension part, 100: radiation protection system, 101: radiation source device, 102: detector, 110: imaging apparatus, S: surgical field

The invention claimed is:

1. A radiation protection equipment, comprising:
   a first protection sheet arranged on a periphery of a radiation source device and configured to shield radiation and to be foldable;
   a second protection sheet formed separately from the first protection sheet, arranged on a side of an operation table, and configured to shield radiation; and
   a third protection sheet formed separately from the first protection sheet and the second protection sheet, arranged on a periphery of a surgical field so as to expose the surgical field, and configured to shield the radiation.

2. A radiation protection equipment according to claim 1, wherein the third protection sheet includes at least two sheets that are combined so as to expose a rectangular region, and
   wherein the two sheets are formed separately from each other.

3. A radiation protection equipment according to claim 1, wherein the first protection sheet includes a first side surface sheet facing a first side surface of the radiation source device, a second side surface sheet facing a second side surface of the radiation source device, and a back surface sheet facing a back surface of the radiation source device, and
   wherein the first side surface sheet, the second side surface sheet, and the back surface sheet are formed separately from each other.

4. A radiation protection equipment according to claim 1, further comprising a sheet support part configured to support the first protection sheet or the third protection sheet.

5. A radiation protection equipment according to claim 4, wherein the sheet support part includes a first extension part extending in a horizontal direction, a second extension part continued from the first extension part and extending in a vertical direction, and a fixing part fixed to an operation table.

6. A radiation protection system, comprising: an imaging apparatus including a radiation source device and a detector; and the radiation protection equipment of claim 1.

7. A radiation protection equipment, comprising:
   a first protection member configured to shield radiation and including a first side surface member facing a first side surface of a radiation source device, a second side surface member facing a second side surface of the radiation source device, and a back surface member facing a back surface of the radiation source device; and
a second protection member formed separately from the first protection member, arranged on a periphery of a surgical field so as to expose the surgical field, and configured to shield the radiation.

8. A radiation protection system, comprising:
an imaging apparatus including a radiation source device and a detector; and
the radiation protection equipment of claim 7.

\* \* \* \* \*